US00PP26203P3

(12) United States Plant Patent
Zaiger et al.

(10) Patent No.: US PP26,203 P3
(45) Date of Patent: Dec. 15, 2015

(54) INTERSPECIFIC TREE NAMED 'AMBER GLO'

(50) Latin Name: **Interspecific *Prunus* species**
Varietal Denomination: AMBER GLO

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 95 days.

(21) Appl. No.: 13/999,864

(22) Filed: Mar. 31, 2014

(65) Prior Publication Data

US 2015/0282402 P1 Oct. 1, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Heavy and regular bearer of fruit.
3. Fruit with attractive yellow skin color.
4. Fruit with good handling and shipping quality.
5. Fruit with very good flavor and eating quality.
6. Fruit with an average 18.0° Brix.

1 Drawing Sheet

Botanical designation:
Interspecific *Prunus* species.
Variety denomination: 'AMBER GLO'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecifics, cherry and nectarine trees, which are known to us, and mentioned herein, 'Dapple Fire' Interspecific (U.S. Plant Pat. No. 12,409), 'Fall Fiesta' Interspecific (U.S. Plant Pat. No. 22,428), our proprietary interspecific seedlings '178LM74', '125LE383', '347LU404', the proprietary nectarine seedling '182GE276' and our proprietary cherry seedling '101EB486'.

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species; *Prunus armeniaca, Prunus salicina, Prunus avium, Prunus persica* and *Prunus persica* var. nucipersica. The present variety was selected as a first generation cross between our proprietary non-patented interspecific seedlings with the field identification numbers '178LM74' and '347LU404'. The seed parent (178LM74) originated from the cross of our proprietary non-patented interspecific seedling '125LE383' with our non-patented proprietary cherry seedling '101EB486'. The pollen parent (347LU404) originated from the cross of our non-patented proprietary genetic dwarf nectarine seedling '182GE276' with 'Dapple Fire' Interspecific (U.S. Plant Pat. No. 12,409). We budded a large number of these seedlings to older 'Nemaguard' Rootstock (non-patented) trees to induce earlier fruit production for evaluation. Under close and careful observation the present seedling exhibited desirable fruit and tree characteristics and was selected in 2009 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree, [(Plum×plumcot)×cherry]×[Nectarine×(Plum×Plum nectarine)×(Peach×PlumPeach)] is of large size, vigorous, upright growth and a regular and productive bearer of medium size, yellow flesh, freestone fruit with very good flavor and eating quality. The fruit is further characterized by its attractive yellow skin, by holding firm on the tree 2 weeks after maturity (shipping ripe) and having good storage and shipping quality. In comparison to its non-patented interspecific seed parent (178LM74) the fruit of the new variety is larger in size and is approximately 90 days later in maturity. In comparison to its non-patented interspecific pollen parent (347LU404) the tree of the new variety has green leaves compared to red leaves and the fruit has glabrous skin compared to pubescent. In comparison to the commercial variety 'Fall Fiesta' Interspecific (U.S. Plant Pat. No. 22,428) the fruit of the new variety has yellow skin compared to blue black and is approximately 6 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken-shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color published in 1958.

Tree:

*Size.*—Large, pruned to 3 to 3.5 meters in height and width for economical harvesting of fruit. Varies with different cultural practices.

*Vigor.*—Vigorous, tree growth of approximately 1.5 to 2 meters the first growing season. Varies with cultural practices, soil type, fertility and climatic conditions.

*Form.*—Upright growth, usually pruned to vase shape.

*Branching habit.*—Upright, crotch angle approximately 30°, increases with heavy crop load.

*Productivity.*—Productive, thinning and spacing of fruit desirable for market size.

*Bearer.*—Regular, adequate fruit set 4 consecutive years. No alternate bearing observed.

*Fertility.*—Self-sterile, pollinator required.

*Density.*—Medium dense, usually pruned to vase shape to increase sunlight and air movement to center of tree to enhance fruit quality and health of fruit spurs.

*Hardiness.*—Hardy in all stone fruit growing areas of California. Tree grown in USDA Hardiness Zone 9. Winter chilling requirement is approximately 900 hours at or below 45° F.

Trunk:

*Size.*—Medium to large. Average circumference 53.3 cm at 22.9 cm above ground level on a 6 year old tree.

*Stocky.*—Medium stocky.

*Texture.*—Medium shaggy, becomes rougher with age.

*Color.*—Varies from 10YR 4/2 to 2.5Y 4/2.

Branches:

*Size.*—Medium stocky. Average circumference 10.4 cm at 1.2 meters above ground. Crotch angle approximately 30°, increases with heavy crop load.

*Surface texture.*—New growth relatively smooth. Mature growth medium rough, roughness increases with age.

*Lenticels.*—Size — medium. Average number 57 in a 25.8 sq cm section. Average length 4.0 mm. Average width 1.4 mm. Color varies from 2.5Y 6/6 to 2.5Y 6/8.

*Color.*—New growth varies from 5GY 4/6 to 5GY 4/8. Old growth varies from 10YR 2/2 to 2.5Y 2/2, varies with age of growth.

Leaves:

*Size.*—Medium. Average length 81.5 mm. Average width 32.5 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins. Lower surface relatively smooth except for small ridges created by midrib and pinnate venation. Both upper and lower surfaces glabrous.

*Petiole.*—Average length 12.0 mm. Average width 1.1 mm. Longitudinally grooved. Surface — glabrous. Color varies from 5GY 5/8 to 5GY 5/4.

*Glands.*—Type — globose. Size — small. Average length 0.4 mm. Average diameter 0.2 mm. Average number 2, varies from 1 to 3. Located primarily on the upper portion of the petiole and the base of the leaf blade. Color varies from 5YR 3/4 to 2.5YR 3/4.

*Stipules.*—Average number 2. Average length 1.8 mm. Edges — pectinate. Color varies from 2.5YR 4/6 to 2.5YR 3/4.

*Color.*—Upper surface varies from 10Y 4/6 to 5GY 4/4. Lower surface varies from 2.5GY 5/4 to 5GY 5/4. Midvein color 7.5Y 7/4.

Flower buds:

*Size.*—Medium. Average length 9.5 mm. Average diameter 5.3 mm.

*Hardiness.*—Hardy with respect to California winters.

*Form.*—Conical, becoming elongated as it matures.

*Pedicel.*—Size — medium to large. Average length 10.1 mm. Average width 0.6 mm. Color varies from 10Y 6/8 to 2.5GY 6/6. Surface — glabrous.

*Color.*—N 9.5/ (white).

*Number of buds per spur.*—Average 9, varies from 7 to 10. Varies with age of spur.

Flowers:

*Blooming period.*—Date of First Bloom Mar. 4, 2013. Date of Petal Fall Mar. 12, 2013, varies slightly with climatic conditions.

*Size.*—Medium. Average height 11.0 mm. Average diameter 18.8 mm.

*Petals.*—Number — normally 5, alternately arranged to sepals. Size — medium. Average length 9.1 mm. Average width 6.8 mm. Form — globose, narrows at point of attachment. Margin — sinuate. Arrangement — free. Both upper and lower surfaces glabrous. Color N 9.5/ (white).

*Sepals.*—Number — normally 5, alternately arranged to petals. Size — small to medium. Average length 3.1 mm. Average width 2.4 mm. Shape — triangular, apex rounded. Margin — entire. Both upper and lower surfaces glabrous. Color — upper surface varies from 2.5GY 5/8 to 5GY 5/8. Lower surface varies from 2.5GY 6/8 to 5GY 5/6.

*Stamens.*—Average number per flower 28, varies from 27 to 30. Average filament length 8.3 mm. Filament color N 9.5/ (white). Anther color varies from 10YR 6/10 to 2.5Y 7/10.

*Pollen.*—Present, self-sterile, pollinator required. Color varies from 2.5Y 7/10 to 2.5Y 6/10.

*Pistil.*—Number — normally 1. Surface — glabrous. Average length 8.5 mm. Position of stigma approximately 1.0 mm below anthers. Color varies from 2.5GY 8/6 to 2.5GY 7/6.

*Fragrance.*—Heavy aroma.

*Color.*—N 9.5/ (white).

*Pedicel.*—Average length 12.4 mm. Average width 0.6 mm. Color varies from 10Y 6/6 to 2.5GY 6/6. Surface — glabrous.

*Number flowers per flower bud.*—Average number 3, varies from 1 to 4.

Fruit:

*Maturity when described.*—Firm ripe.

*Date of first picking.*—Sep. 24, 2013.

*Date of last picking.*—Oct. 1, 2013, varies slightly with climatic conditions.

*Size.*—Medium. Average diameter axially 67.1 mm. Average transversely in suture plane 57.3 mm. Average weight 122.1 grams, varies slightly with fertility of the soil, amount of thinning and climatic conditions.

*Form.*—Elongated.

*Suture.*—Nearly smooth, extends from base to apex.

*Ventral surface.*—Nearly smooth.

*Apex.*—Rounded.

*Base.*—Flat to slightly retuse.

*Stem cavity.*—Rounded to slightly elongated in suture plane. Average depth 4.3 mm. Average diameter 2.3 mm.

Stem:

*Size.*—Medium to large. Average length 16.7 mm. Average diameter 1.7 mm.

*Color.*—Varies from 5GY 7/6 to 5GY 7/8.

Skin:

*Thickness.*—Medium.

*Surface.*—Smooth.

*Bloom.*—Moderate amount, completely covered.

*Tendency to crack.*—None.

*Color.*—Varies from 10YR 7/10 to 10YR 7/12.

*Tenacity.*—Tenacious to flesh.

*Astringency.*—None.

Flesh:

*Ripens.*—Evenly.

*Texture.*—Firm, meaty.

*Fibers.*—Few, small, tender.

*Firmness.*—Firm, comparable to commercial varieties.

*Aroma.*—Moderate.

*Amydgalin.*—Undetected.

*Eating quality.*—Very good.

*Flavor.*—Very good, good balance between acid and sugar.

*Juice.*—Moderate amount, enhances flavor.

*Brix.*—Average Brix 18.0°, varies slightly with amount of fruit per tree and climatic conditions.

*Color.*—Varies from 10YR 7/10 to 10YR 8/8.

*Pit cavity.*—Average length 33.2 mm. Average width 18.3 mm. Average depth 5.7 mm. Color varies from 5YR 6/10 to 10YR 8/6.

Stone:

*Type.*—Freestone.

*Size.*—Medium to large. Average length 31.2 mm. Average width 16.3 mm. Average thickness 9.0 mm.

*Form.*—Ovoid.

*Base.*—Flat.

*Apex.*—Pointed. Average length 2.1 mm.

*Surface.*—Lightly pitted throughout.

*Sides.*—Unequal, one side extending further outward from suture plane.

*Ridges.*—A small narrow ridge on each side of suture plane extending from base to apex.

*Tendency to split.*—None.

*Color.*—Varies from 2.5YR 4/6 to 2.5YR 5/8 when dry.

Kernel:

*Size.*—Medium to large. Average length 16.7 mm. Average width 8.9 mm. Average depth 4.4 mm.

*Form.*—Ovoid.

*Viability.*—Viable, complete embryo development.

*Skin color.*—Varies from 10YR 5/6 to 10YR 5/8.

Use:

*Dessert.*—Market — local and long distance.

Keeping quality: Good, held firm 3 weeks at 38° to 42° F. without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

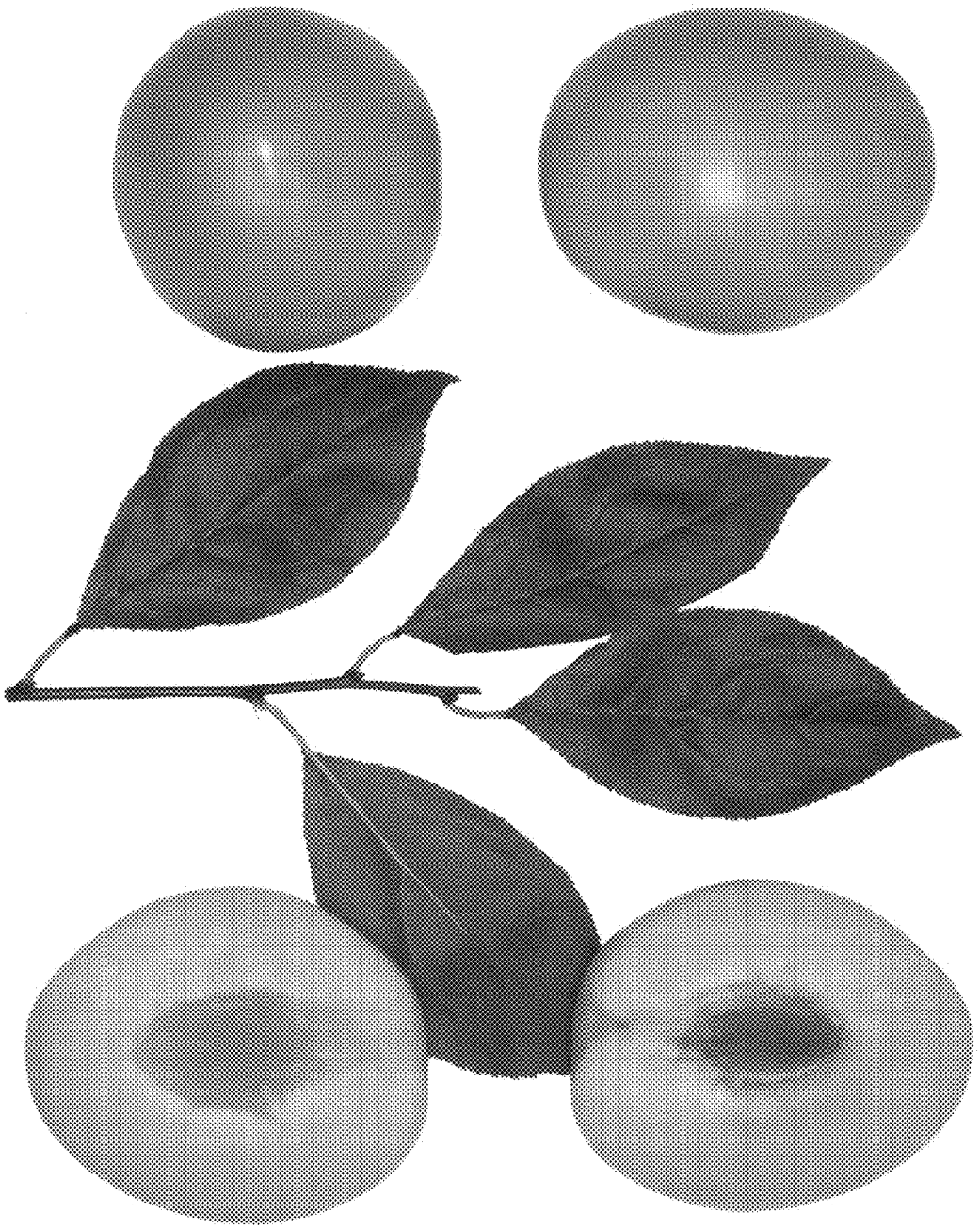

* * * * *